United States Patent [19]

Satomura et al.

[11] Patent Number: 4,914,219

[45] Date of Patent: Apr. 3, 1990

[54] PROCESS FOR PREPARING ZINC SALT OF SALICYLIC ACID COMPOUND

[75] Inventors: Masato Satomura; Ken Iwakura, both of Shizuoka, Japan

[73] Assignee: Fuji Photo Film Co., Ltd., Kanagawa, Japan

[21] Appl. No.: 256,940

[22] Filed: Oct. 13, 1988

[30] Foreign Application Priority Data

Oct. 14, 1987 [JP] Japan .................................. 62-259109

[51] Int. Cl.$^4$ ............................................. C07F 3/06
[52] U.S. Cl. ................................................... 556/132
[58] Field of Search ......................................... 556/132

[56] References Cited

U.S. PATENT DOCUMENTS 1,933,520 7/1931 Bruson .................................. 556/132
2,113,496 2/1932 Roon et al. .......................... 556/132

OTHER PUBLICATIONS

Pavia et al. *Introduction to Organic Laboratory Techniques,* New York; Saunders College Publishing, 1982.
English abstract of published Japanese application 63-41183(A), Ikeda. (2-22-88).

*Primary Examiner*—Paul F. Shaver
*Attorney, Agent, or Firm*—Sughrue, Mion, Zinn, Macpeak & Seas

[57] ABSTRACT

A process for preparing a zinc salt of a salicylic acid compound which comprises reacting a salicylic acid compound and/or an alkali metal salt thereof with a zinc compound, wherein the reaction is carried out in a mixture of water and an organic solvent, and wherein the organic solvent has a water solubility of not more than 0.1 g/100 g water at 25° C. and in which the zinc salt has a solubility of not less than 10 g/100 g organic solvent at 25° C. The process achieves improved workability in collection of the product and improved yield and purity of the product.

11 Claims, No Drawings

PROCESS FOR PREPARING ZINC SALT OF SALICYLIC ACID COMPOUND

FIELD OF THE INVENTION

This invention relates to a process for preparing a zinc salt of a salicylic acid compound, which salt is useful as an electron-accepting compound in two component recording materials, such as pressure-or heat-sensitive recording materials. More particularly, the present invention relates to a process for preparing the zinc salt compound, which process achieves improved workability in collection of the product and improved yield and purity of the product.

BACKGROUND OF THE INVENTION

It is known that a metal salt of a salicylic acid compound can be used as an electron-accepting compound in recording materials using a combination of an electron-donating colorless dye and an electron-accepting compound, as described, for example, U.S. Pat. Nos. 3,864,146, 3,983,292, 4,134,847, 4,234,212 and 4,289,332, and JP-B-58-38118 (the term "JP-B" as used herein means an "examined Japanese patent publication").

Known processes for preparing a zinc salt of a salicylic acid compound include methods in which a salicylic acid compound or its alkali metal salt is reacted with a zinc compound in water or in the absence of a solvent. However, these conventional methods were not satisfactory in workability or yield or purity of the product.

SUMMARY OF THE INVENTION

One object of this invention is to provide a process for preparing a zinc salt of a salicylic acid compound whereby the preparation process can achieve improvements in workability in collection of the product and in improved yield and purity of the product.

It has now been found that the above object of this invention can be accomplished by carrying out the reaction between a salicylic acid compound and/or an alkali metal salt thereof and a zinc compound in a mixture of water and an organic solvent wherein the organic solvent has a water solubility of not more than 0.1 g/100 g water at 25° C. and in which the zinc salt has a solubility of not less than 10 g/100 g organic solvent at 25° C.

In carrying out the reaction in accordance with the present invention, the desired zinc salts which are to be produced can easily be obtained in the form of a solution in the organic solvent, and they can be isolated simply by removing the organic solvent from the solution. If desired, the produced zinc salt as dissolved in the organic solvent may be used as such. Further, the desired zinc salts can be obtained in the form of a dispersion by treating by means of a dispersing machine with media after removing the organic solvent from the resulting reaction solution. If the reaction is conducted using a water-soluble organic solvent, i.e., a solvent having a water-solubility greater than 0.1 g/100 g water, the produced zinc salt is not satisfactorily dispersed in the reaction mixture and is apt to form oil-soluble masses, thus seriously deteriorating workability in collection of the product.

DETAILED DESCRIPTION OF THE INVENTION

The salicylic acid compound which can be used as a reactant in the present invention can be represented by the formula (I):

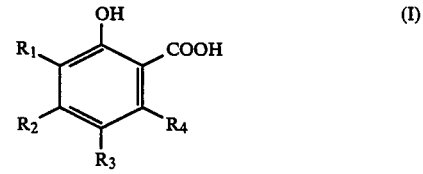

wherein $R_1$, $R_2$, $R_3$, and $R_4$, which may be the same or different, each represents a hydrogen atom, a substituted or unsubstituted alkyl group (preferably from 1 to 30 carbon atoms, and more preferably from 1 to 20 carbon atoms), a substituted or unsubstituted alkoxy group (preferably from 1 to 20 carbon atoms), a substituted or unsubstituted aryl group (preferably from 6 to 20 carbon atoms, and more preferably from 6 to 10 carbon atoms), or a halogen atom.

In formula (I), substituents for $R_1$, $R_2$, $R_3$, and $R_4$ include an alkyl group, an aryl group, an alkoxy group, an aryloxy group, a halogen atom, an acylamino group, an aminocarbonyl group, a cyano group, preferably a phenyl group, an alkyl substituted phenyl group or an aralkyl substituted phenyl group.

Specific examples of the groups as represented by $R_1$, $R_2$, $R_3$, and $R_4$ include a hydrogen atom, methyl, ethyl, isopropyl, t-butyl, t-octyl, nonyl, dodecyl, cyclohexyl, benzyl, α-methylbenzyl, α,α-dimethylbenzyl, α-tolylethyl, α-tolylisopropyl, α-(α-methylbenzyl)-phenylethyl, (mesitylmethyl)benzyl, phenyl, and naphthyl groups, a chlorine atom.

From the standpoint of water-insolubility of the zinc salt of the salicylic acid compounds, the salicylic acid compounds of formula (I) preferably contain at least 13 carbon atoms, particularly at least 17 carbon atoms, in total.

Specific examples of these salicylic acid compounds are 5-phenylsalicylic acid, 5-benzylsalicylic acid, 3,5-di-t-octylsalicylic acid, 3,5-bis(u-methylbenzyl)salicylic acid, 3,5-bis(α,α-dimethylbenzyl)-salicylic acid, 3-(α-methylbenzyl)-5-phenylsalicylic acid, 3-(α,α-dimethylbenzyl)-5-phenylsalicylic acid, 3-phenyl-5-(α-methylbenzyl)salicylic acid, 3-phenyl-5-(α,α-dimethylbenzyl)-salicylic acid, 3-(α-methylbenzyl)-5-cyclohexylsalicylic acid, 3,5-bis(α-tolylethyl)salicylic acid, 5-(1,3-diphenylbutyl)salicylic acid, 5-[α-(α-methylbenzyl)phenylethyl]salicylic acid, 4-(mesitylmethyl)benzylsalicylic acid, 4-[3-[4-(mesitylmethyl)benzyl]-2,4,6-trimethylbenzyl]benzylsalicylic acid, 3(1-benzylphenylethyl)-5-α-methylbenzylsalicylic acid, 3-α-methylbenzyl-5-(1-bezylphenylethyl)salicylic acid and 3,5-bis(1-benzylphenylethyl)salicylic acid, more preferably 3,5-di-t-octylsalicylic acid, 3,5-bis(α-methylbenzyl)salicylic acid and 3,5-bis(α,α-dimethylbenzyl)salicyclic acid.

Specific examples of a alkali metal salt of the salicylic acid compound which can be used as a reactant include the lithium, sodium or potassium salt, preferably the sodium or potassium salt.

The zinc compound which can be used in the present invention as a reactant is any zinc compound which can react with the salicylic acid compound or alkali metal salt thereof to yield a zinc salt of a salicylic acid compound, and includes zinc oxide, zinc hydroxide, zinc carbonate, zinc sulfate, zinc chloride, etc. The zinc compounds may be used alone or as a mixture thereof.

Of the above-described reactants, a combination of an alkali metal salt of a salicylic acid compound and a zinc salt, e.g., zinc sulfate and zinc chloride, is preferred in view of the facility in working-up the zinc salt product after it is formed.

The organic solvent to be used in the reaction has a water solubility of not more than 0.1 at 25° C., and has such dissolving power that the above-described zinc salt of the salicylic acid compound has a solubility in the organic solvent of 10 or more at 25° C. The term "solubility" as used herein indicates a weight (g) of a solute which can be dissolved in 100 g of a solvent and can be determined in a usual manner.

Examples of such an organic solvent include aromatic compounds and halogenated organic compounds, e.g., toluene, xylene, trichloroethylene, chlorobenzene, chlorinated paraffin, diisopropylnaphthalene, nucleus-substituted diphenylmethane, etc. From the viewpoint of evaporation loss during the preparation, preferred are aromatic compounds substituted with one or more of an alkyl group, an alkoxy group, a halogen atom, etc., and whose boiling point is no lower than 100° C. In cases where the product is subjected to drying to recover a powder, organic solvents having a boiling point of not more than 150° C. are desirable. The organic solvents may be used alone or as a mixture thereof.

The organic solvents are preferably used in an amount of from 0.05 to 15 parts by weight, more preferably from 1 to 10 parts by weight, per part by weight of the zinc salt product.

The reaction temperature preferably ranges from 10 to 100° C., more preferably from 20 to 90° C.

In the process for producing the zinc salt of salicylic acid compounds in accordance with the present invention, it is preferred that water-soluble inorganic materials and the like are removed in a liquid-liquid separation procedure after being reacted with a zinc compound.

In the step of removing the organic solvent used from the reaction solution, the treatment temperature is not particularly limited, but it is preferred that the organic solvent is removed by distillation under reduced pressure. In the above case, a slight amount of water may be distilled off with the organic solvent.

Where the zinc salts of salicylic acid compound produced in accordance with the present invention are directly dispersed, a dispersing machine using media, such as a sand mill, a dyno mill, an attritor, a ball mill, etc. is preferably used. Of these dispersing machines, a dispersing machine utilizing a high rotating speed such as a sand mill or a dyno mill is advantageous in that the reaction mixture can be continuously treated and the treated mixture can be directly charged into tank of coating machine. In the dispersing step, various media may be used. In general, a flint stone, an Ottawa sand, a steel ball, ceramics, a high-alumina ball, a zircon, a glass ball, etc. Among them, media having a spherical form are advantageous in workability or maintainability. From the viewpoint of preventing a viscosity of the reaction product, a treatment with the dispersing machine is preferably carried out at a temperature of 30° C. or less.

An inorganic pigment, a dispersing agent, a resin, a binder, etc. may be added in the reaction mixture at the dispersing step.

Examples of the inorganic pigments include a natural or synthetic inorganic pigment. Specific examples of these inorganic pigments are barium sulfate, barium carbonate, calcium carbonate, gypsum, clay, silica, fine particle silicic acid, diatomaceous earth, talc, basic magnesium carbonate, alumina white, zinc white, lithopone, calcium silicate, synthetic calcium carbonate, magnesium carbonate, lime carbonate, aluminium hydroxide, etc. These inorganic pigments are used in an amount of from about 5 to 500 parts per 10 parts of the desired zinc salt.

Examples of the dispersing agents include a low molecular oligomer or polymer having a polar group such as a phospholic acid radical, a sulfo group, a carboxyl group or salt thereof. Specific examples of these dispersing agents are a sodium salt of dialkylsulfosuccinic acid ester, a sodium salt of naphthalinesulfonic acid-formaline condensate, polystyrene sulfonate, sulfonated styrene oligomer, ammonium salt of sulfonated styrene oligomer. A binder such as polyvinyl alcohol as stated below may be used. These dispersing agents are used in an amount of from about 0.5 to 45 parts per 100 parts of the desired zinc salt.

The binder is selected in view of the intimate contact between a recording layer and a support, the membrane strength of the recording layer, etc.

Examples of the water-soluble binder includes a natural high molecular compound such as a protein (e.g., gelatin, albumine or casein), a cellulose (e.g., carboxymethyl cellulose or hydroxyethyl cellulose) and a sacchalose (e.g., ager-ager, sodium alginate, carboxymethyl starch or gum arabic); a synthetic high molecular compound such as polyvinyl alcohol, polyvinyl pyrrolidone, polyacrylic acid, polyacrylic amide, styrene-butadiene-methacrylic acid copolymer, acrylonitrile-butadieneacrylic acid copolymer, and styrene-maleic anhydride copolymer, or latexes.

It is important to control a volume average particle size at the dispersing step. The particle size is preferably finely ground to 4 μm or less to improve the color developing ability, color forming speed, etc.

The dispersion obtained above is coated to a support such as a base paper, a wood-free paper, a synthetic paper or a neutral paper.

The present invention will now be illustrated in greater detail by way of the following Examples, but it should be understood that the present invention is not limited thereto.

EXAMPLE 1

In 200 ml of water were dissolved 17 g of 3,5-bis(α-methylbenzyl)salicylic acid and 2.0 g of sodium hydroxide. To the solution was added 50 ml of toluene, and the mixture was heated to 70° C. while stirring. Then, a solution of 7.2 g of zinc sulfate heptahydrate in 100 ml of water was added dropwise thereto over a period of 10 minutes. After stirring for 30 minutes, a toluene solution containing 18.6 g of zinc 3,5-bis(α-methylbenzyl)-salicylate was obtained by liquid-liquid separation, i.e., pouring off. The separated toluene solution did not contain 3,5-bis(α-methylbenzyl)salicylic acid.

To the toluene solution was added water, and the toluene was removed as the water azeotrope therefrom by distillation under reduced pressure while stirring to obtain a dispersion of zinc 3,5-bis(α-methylbenzyl)-salicylate.

EXAMPLE 2

An aqueous solution (300 ml) containing 7.2 g of zinc sulfate heptahydrate was heated to 70° C. while stirring. To the solution was added dropwise 75 ml of a xylene solution containing 18.0 g of sodium 3,5-bis($\alpha$-methylbenzyl)salicylate over a period of 10 minutes. The mixture was stirred for 30 minutes and then subjected to liquid-liquid separation to obtain a xylene solution containing 18.4 g of zinc 3,5-bis($\alpha$-methylbenzyl)salicylate.

EXAMPLE 3

In 200 ml of water were dissolved 17 g of 3,5-bis($\alpha$-methylbenzyl)salicylic acid and 2.0 g of sodium hydroxide. To the solution was added 25 ml of diisopropylnaphthalene, and the mixture was heated to 80° C. and stirred. Then, a solution of 3.5 g of zinc chloride in 100 ml of water was added thereto dropwise over 10 minutes. After stirring for 30minutes followed by liquid-liquid separation, a diisopropylnaphthalene solution containing 18.4 g of zinc 3,5-bis($\alpha$-methylbenzyl)salicylate was obtained.

COMPARATIVE EXAMPLE

The same reaction procedure as in Example 1 was repeated, except for using no toluene. When the reaction mixture was stirred for 30 minutes, an insoluble matter was precipitated, but the mixture was syrupy. Upon cooling, the product solidified to form a mass. The crystals thus formed were collected by filtration, but the workability was very poor since a portion of the crystals adhered to the wall of the reactor. The filter cake was washed with water and dried to obtain 18.1 g of zinc 3,5-bis($\alpha$-methylbenzyl)-salicylate. This product was found to contain trace amounts of 3,5-bis(u-methylbenzyl)salicylic acid and inorganic salts.

EXAMPLE 4

An aqueous solution (300 ml) containing 7.2gg of zinc sulfate heptahydrate wa heated to 70° C. while stirring. To the solution was added dropwise 75 ml of xylene solution containing 18.0 g of sodium 3,5-bis($\alpha$-methylbenzyl)salicylate over a period of 10 minutes. The mixture was stirred for 30 minutes and then subjected to a liquid-liquid separation to obtain a xylene solution containing 18.4 g of zinc 3,5-bis($\alpha$-methylbenzyl)salicylate.

To the resulting xylene solution was added 500 parts of calcium carbonate, 80 parts of zinc oxide, 1 part of sodium hexametaphosphate and 1,000 parts of water, and the xylene was removed as the water azeotrope therefrom by distillation under reduced pressure. Then, the solution was dispersed by means of sand grinder to 3 $\mu$m of average particle size to obtain a dispersion of zinc 3,5-bis($\alpha$-methylbenzyl)salicylate.

From the foregoing Examples 1 to 4 in comparison with the Comparative Example, it can be seen that the process in accordance with the present invention is superior in workability and yield and purity of the desired product.

While the invention has been described in detail and with reference to specific embodiments thereof, it will be apparent to one skilled in the art that various changes and modifications can be made therein without departing from the spirit and scope thereof.

What is claimed is:

1. A process for preparing a water dispersion of a zinc salt of a salicylic acid compound comprising the steps of:

(1) reacting:
    (A) at least one compound selected from the group consisting of a salicylic acid compound represented by formula (I), an alkali metal salt of a salicylic acid Compound represented by formula (I) and a mixture thereof:

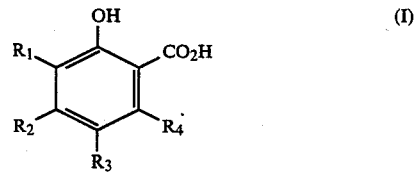

wherein $R_1$, $R_2$, $R_3$ and $R_4$, are the same or different consisting of a hydrogen atom, a substituted alkyl group, an unsubstituted alkyl group, a substituted alkoxy group, an unsubstituted alkoxy group, a substituted aryl group, an unsubstituted aryl group and a halogen atom; with (B) a zinc compound selected from the group consisting of zinc oxide, zinc hydroxide, zinc carbonate, zinc sulfate and zinc chloride,
    wherein the reaction is carried out in a mixture of water and an organic solvent, wherein said organic solvent has a water solubility of not more than 0 1 g/100 g of water at 25° C., and wherein the resulting zinc salt product has a solubility of not less than 10 g/100 g or organic solvent at 25° C.,
    (2) removing a water layer from the resulting reaction mixture of step (1) so as to obtain an organic solvent layer containing the resulting zinc salt product;
    (3) admixing water with the resulting organic solvent layer containing the resulting zinc salt product of step (2); and
    (4) removing the organic solvent layer by distillation in the presence of said added water so as to obtain said water dispersion.

2. The according to claim 1, wherein said unsubstituted alkyl group has from 1 to 30 carbon atoms, said substituted alkyl group comprises an alkyl group having from 1 to 30 carbon atoms, said unsubstituted alkoxy group has from 1 to 20 carbon atoms, said substituted alkoxy group comprises an alkoxy group having from 1 to 20 carbon atoms, said unsubstituted aryl group has from 6 to 20 carbon atoms and said substituted aryl group comprises an aryl group having from 6 to 20 carbon atoms.

3. The process according to claim 1, wherein said organic solvent has a boiling point higher than 100° C. and said organic solvent is an aromatic compound substituted with a member selected from the group consisting of an alkyl group, an alkoxy group, and a halogen atom.

4. A process as claimed in claim 2, wherein said salicylic acid compound contains at least 13 carbon atoms in total.

5. A process as claimed in claim 1, wherein an alkali metal salt of a salicyclic acid compound is reacted with a zinc compound which is selected from the group consisting of zinc sulfate and zinc chloride.

6. A process as claimed in claim 1, wherein said process further comprises a step of drying to obtain a powder.

7. A process as claimed in claim 6, wherein said organic solvent has a boiling point of no lower than 150° C.

8. A process as claimed in claim 1, wherein said organic solvent is used in an amount of from 0.05 to 15 parts by weight per part by weight of the zinc product.

9. A process as claimed in claim 1, wherein said organic solvent is used in an amount of from 1 to 10 parts by weight per part by weight of the zinc product.

10. A process as claimed in claim 1, wherein, said reacting is carried out at a temperature of from 10°C. to 100° C.

11. A process as claimed in claim 1, wherein said reacting is carried out at a temperature of from 2020 C. to 90° C.

* * * * *